United States Patent
King et al.

(10) Patent No.: US 8,343,100 B2
(45) Date of Patent: Jan. 1, 2013

(54) SURGICAL SYSTEM HAVING A NON-INVASIVE FLOW SENSOR

(75) Inventors: Nicolei R. King, Aliso Viejo, CA (US); David L. Williams, Newport Beach, CA (US)

(73) Assignee: Novartis AG, Basel (CH)

( * ) Notice: Subject to any disclaimer, the term of this patent is extended or adjusted under 35 U.S.C. 154(b) by 1744 days.

(21) Appl. No.: 11/437,302

(22) Filed: May 19, 2006

(65) Prior Publication Data

US 2007/0232991 A1  Oct. 4, 2007

Related U.S. Application Data

(63) Continuation-in-part of application No. 11/391,748, filed on Mar. 29, 2006.

(51) Int. Cl.
- A61M 37/00 (2006.01)
- A61M 1/00 (2006.01)
- F04B 43/12 (2006.01)
- G01F 1/20 (2006.01)

(52) U.S. Cl. ......... 604/131; 604/30; 604/35; 417/477.2; 73/861.18

(58) Field of Classification Search ............... 604/30, 604/131, 118, 246, 31, 34, 35; 417/477.6, 417/477.2; D14/496; 73/861.27–861.28, 73/861.18
See application file for complete search history.

(56) References Cited

U.S. PATENT DOCUMENTS

| | | |
|---|---|---|
| 4,395,258 A | 7/1983 | Wang et al. |
| 4,479,761 A | 10/1984 | Bilstad et al. |
| 4,493,695 A | 1/1985 | Cook |
| 4,592,741 A | 6/1986 | Vincent |
| 4,627,833 A | 12/1986 | Cook |
| 4,704,909 A * | 11/1987 | Grahn et al. ............ 73/862.043 |
| 4,713,051 A | 12/1987 | Steppe et al. |
| 4,758,238 A | 7/1988 | Sundblom et al. |
| 4,773,897 A | 9/1988 | Scheller et al. |
| 4,787,070 A | 11/1988 | Suzuki et al. |
| 4,790,816 A | 12/1988 | Sundblom et al. |
| 4,798,580 A | 1/1989 | DeMeo et al. |
| 4,842,584 A | 6/1989 | Pastrone |
| 5,078,149 A | 1/1992 | Katsumata et al. |
| 5,165,412 A | 11/1992 | Okazaki |
| 5,265,614 A | 11/1993 | Hayakawa et al. |
| 5,267,956 A | 12/1993 | Beuchat |
| 5,273,517 A * | 12/1993 | Barone et al. ................... 494/37 |
| 5,282,787 A * | 2/1994 | Wortrich ......................... 604/30 |
| 5,364,342 A * | 11/1994 | Beuchat et al. ................. 604/30 |
| 5,463,906 A * | 11/1995 | Spani et al. ................. 73/861.27 |
| 5,499,969 A | 3/1996 | Beuchat et al. |
| 5,514,102 A | 5/1996 | Winterer et al. |
| 5,746,241 A | 5/1998 | Stedman |

(Continued)

FOREIGN PATENT DOCUMENTS

CA  2127039  3/1996

(Continued)

*Primary Examiner* — Kevin C Sirmons
*Assistant Examiner* — Bradley Thomas, Jr.

(57) ABSTRACT

A surgical system having a console that receives a cassette with a rigid fluid channel formed into a rigid plastic component or housing. The housing serves as a substrate for an elastomeric acoustic coupling that can be formed on the housing outside of the fluid channel. The acoustic transducer is elastically mounted within the console, such as on a spring, so as to provide a relatively constant force between the transducer and the acoustic coupling when the cassette is installed in the console.

20 Claims, 6 Drawing Sheets

U.S. PATENT DOCUMENTS

| | | | |
|---|---|---|---|
| 5,747,824 A | 5/1998 | Jung et al. | |
| 6,039,694 A | 3/2000 | Larson et al. | |
| 6,098,466 A | 8/2000 | Shkarlet | |
| 6,171,280 B1 * | 1/2001 | Imazu et al. | 604/118 |
| 6,203,528 B1 * | 3/2001 | Deckert et al. | 604/131 |
| 6,330,831 B1 | 12/2001 | Lynnworth et al. | |
| 6,349,599 B1 | 2/2002 | Lynnworth et al. | |
| 6,511,454 B1 * | 1/2003 | Nakao et al. | 604/31 |
| 6,517,487 B1 | 2/2003 | Mazess et al. | |
| 6,554,822 B1 * | 4/2003 | Holschneider et al. | 604/892.1 |
| 6,599,277 B2 | 7/2003 | Neubert | |
| 6,715,366 B2 | 4/2004 | Ohnishi | |
| 6,820,500 B2 | 11/2004 | Wilda | |
| 6,908,451 B2 | 6/2005 | Brody et al. | |
| 7,062,972 B2 | 6/2006 | Hill | |
| 7,168,930 B2 * | 1/2007 | Cull et al. | 417/477.8 |
| 7,194,919 B2 | 3/2007 | Shkarlet et al. | |
| 7,289,914 B2 | 10/2007 | Hishida et al. | |
| 7,392,144 B2 | 6/2008 | Sorensen et al. | |
| 2002/0108450 A1 | 8/2002 | Ohnishi | |
| 2003/0101826 A1 | 6/2003 | Neubert | |
| 2003/0190244 A1 * | 10/2003 | Davis et al. | 417/477.2 |
| 2003/0195420 A1 | 10/2003 | Mendlein et al. | |
| 2004/0039431 A1 | 2/2004 | Machold et al. | |
| 2004/0050154 A1 | 3/2004 | Machold et al. | |
| 2004/0102707 A1 | 5/2004 | Murkin | |
| 2004/0254469 A1 | 12/2004 | Shkarlet et al. | |
| 2005/0016281 A1 | 1/2005 | Hill | |
| 2005/0069419 A1 | 3/2005 | Cull et al. | |
| 2005/0215901 A1 | 9/2005 | Anderson et al. | |
| 2005/0241411 A1 | 11/2005 | Hishida et al. | |
| 2005/0245888 A1 | 11/2005 | Cull | |
| 2006/0009818 A1 | 1/2006 | Von Arx et al. | |
| 2006/0235303 A1 | 10/2006 | Vaezy et al. | |
| 2007/0005030 A1 | 1/2007 | Hopkins et al. | |
| 2007/0073068 A1 | 3/2007 | Quaedflieg et al. | |
| 2007/0107490 A1 | 5/2007 | Artsyukhovich et al. | |
| 2007/0219494 A1 | 9/2007 | Gao et al. | |
| 2007/0232990 A1 | 10/2007 | Hopkins et al. | |
| 2007/0244427 A1 | 10/2007 | Nazarifar | |
| 2008/0097284 A1 | 4/2008 | Gao et al. | |
| 2008/0240951 A1 * | 10/2008 | Domash et al. | 417/477.2 |
| 2009/0232991 A1 | 9/2009 | Wang et al. | |

FOREIGN PATENT DOCUMENTS

| | | |
|---|---|---|
| EP | 1840533 A1 | 10/2007 |
| EP | 1840534 A1 | 10/2007 |
| EP | 1840534 B1 | 9/2009 |
| EP | 1840533 B1 | 9/2010 |
| JP | 2004257738 A | 9/2004 |
| JP | 2005192890 A | 7/2005 |
| WO | WO 9318802 A1 | 9/1993 |
| WO | WO 03/047652 A1 | 6/2003 |
| WO | WO 2007/117781 A2 | 10/2007 |
| WO | WO 2007/117781 A3 | 10/2007 |

* cited by examiner

SURGICAL SYSTEM HAVING A NON-INVASIVE FLOW SENSOR

This application is a continuation-in-part of U.S. patent application Ser. No. 11/391,748, filed Mar. 29, 2006, currently co-pending.

BACKGROUND OF THE INVENTION

The present invention relates to an ultrasonic flow sensor and more particularly to a surgical system and cassette having an ultrasonic flow sensor.

Conventional ophthalmic surgical instrument systems use vacuum to aspirate the surgical site and positive pressure to irrigate the site. Typically, a cassette is serially connected between the means used to generate pressure and the surgical instrument. The use of cassettes with surgical instruments to help manage irrigation and aspiration flows at a surgical site is well known. U.S. Pat. Nos. 4,493,695 and 4,627,833 (Cook), U.S. Pat. No. 4,395,258 (Wang, et al.), U.S. Pat. No. 4,713,051 (Steppe, et al.), U.S. Pat. No. 4,798,850 (DeMeo, et al.), U.S. Pat. Nos. 4,758,238, 4,790,816 (Sundblom, et al.), and U.S. Pat. Nos. 5,267,956, 5,364,342 (Beuchat) and U.S. Pat. No. 5,747,824 (Jung, et al.) all disclose ophthalmic surgical cassettes with or without tubes, and they are incorporated in their entirety by this reference. Aspiration fluid flow rate, pump speed, vacuum level, irrigation fluid pressure, and irrigation fluid flow rate are some of the parameters that require precise control during ophthalmic surgery.

Prior art devices have used pressure sensors in the aspiration and irrigation lines and calculate fluid flow rates based on the sensed pressure. In the past, measuring of fluid pressures in surgical cassettes has been very precise and as the resistance in the fluid paths is known, fluid flow rates can be calculated reliably from fluid pressure. Recent improvements in the reliability of ultrasonic flow sensors, however, have now made it possible to non-invasively measure fluid flow accurately.

For example, one ultrasonic flow sensor disclosed in U.S. Pat. No. 6,098,466 (Shkarlet) discloses a flow sensor capable of accurately measuring fluid flow in vessels or tubes having decreased sensitivity to flow distribution non-uniformities and decreased overall size by employing multiple angled reflector surfaces which cause incident ultrasonic waves from one or more ultrasonic transducers to pass through the flow volume multiple times and in multiple directions without changing the planar orientation of the ultrasound waves. The wave paths resulting from the multiple reflections and multi-directional illumination of the flow volume decreases the probe's size and sensitivity to spatial distribution non-uniformities. The multiple angled reflector surfaces also permit the transmitting and receiving ultrasonic transducers to be placed close to one another, thereby reducing the overall probe size and making them particularly useful for incorporation in the relatively small fluid flow cassette used in ophthalmic surgery. In order for an ultrasonic flow sensor to work, the transducer must be acoustically coupled to the tubing in which the fluid is flowing so that any air located between the transducer and the tubing is removed. This acoustic coupling is sensitive to the amount of pressure between the transducer and the flow channel being monitored, making a fairly constant force desirable. When the flow channel is mounted on a removable surgical cassette and the transducer located in a surgical console on which the cassette connects, normal manufacturing variation can result in undesirable variation in the amount of force pressing the cassette into the transducer, thereby causing inaccuracies in the flow measurement.

Accordingly, a need continues to exist for a device for assuring a fairly constant force between a flow channel located on a surgical cassette and an ultrasonic flow measuring transducer located on a surgical console.

BRIEF DESCRIPTION OF THE INVENTION

The present invention improves upon the prior art by providing a surgical system having a console that receives a cassette with a rigid fluid channel formed into a rigid plastic component or housing. The housing serves as a substrate for an elastomeric acoustic coupling that can be formed on the housing outside of the fluid channel. The acoustic transducer is elastically mounted within the console, such as on a spring, so as to provide a relatively constant force between the transducer and the acoustic coupling when the cassette is installed in the console.

Accordingly, one objective of the present invention is to provide a surgical cassette having an acoustic coupling.

Another objective of the present invention is to provide a surgical cassette having an acoustic coupling that is formed on the cassette without the use of adhesives.

Yet another objective of the present invention is to provide a surgical system with a cassette having an acoustic coupling that is over molded onto the cassette.

These and other advantages and objectives of the present invention will become apparent from the detailed description, drawings and claims that follow.

DETAILED DESCRIPTION OF THE PREFERRED EMBODIMENTS

Figure 1:
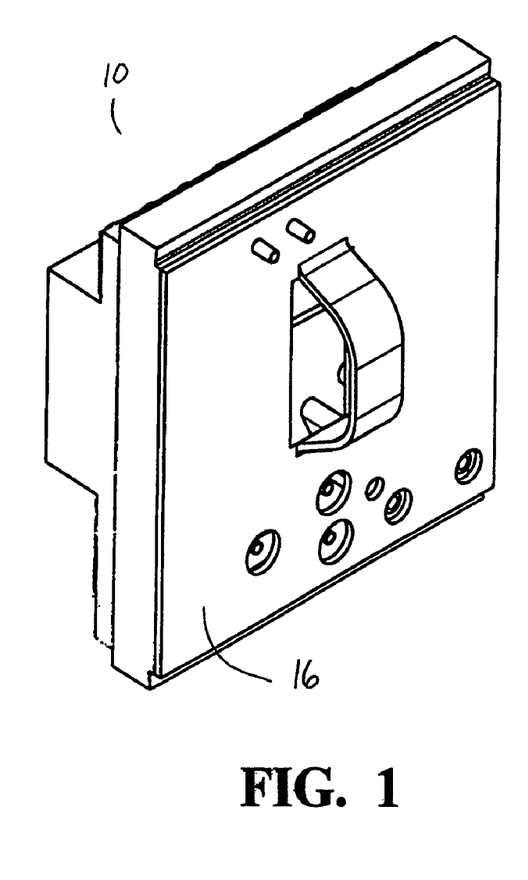
FIG. 1 is a front perspective view of the cassette that may be used with the present invention.
Figure 2:
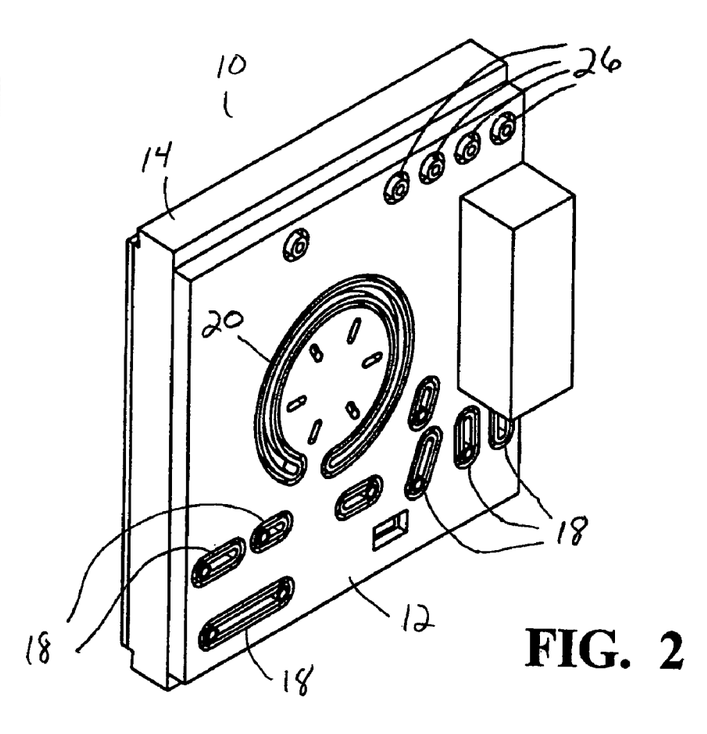
FIG. 2 is a rear perspective view of the cassette that may be used with the present invention.
Figure 3:
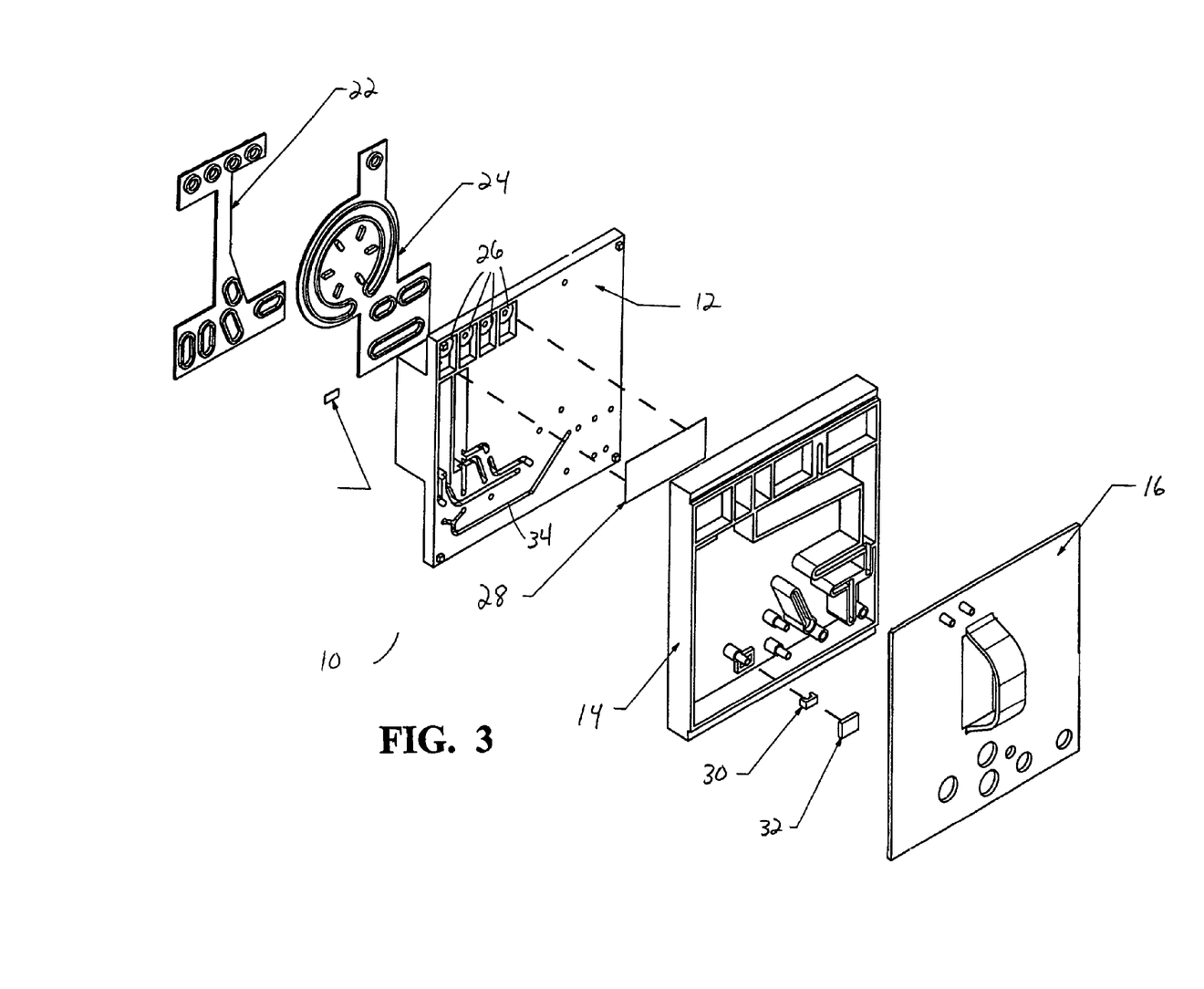
FIG. 3 is an exploded perspective view of the cassette that may be used with the present invention.
Figure 4:
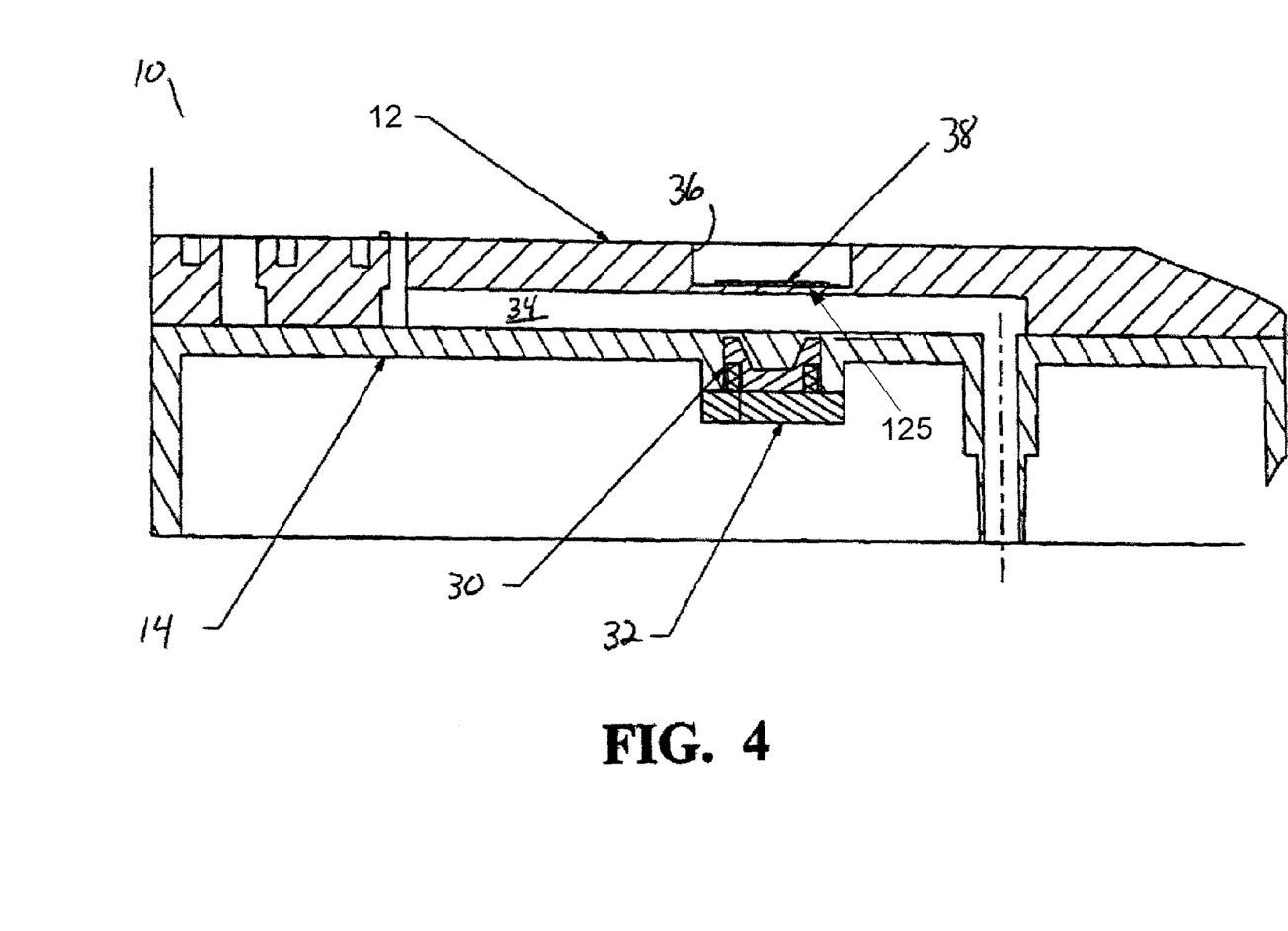
FIG. 4 is a partial cross-sectional view of the cassette that may be used with the present invention.
Figure 5:
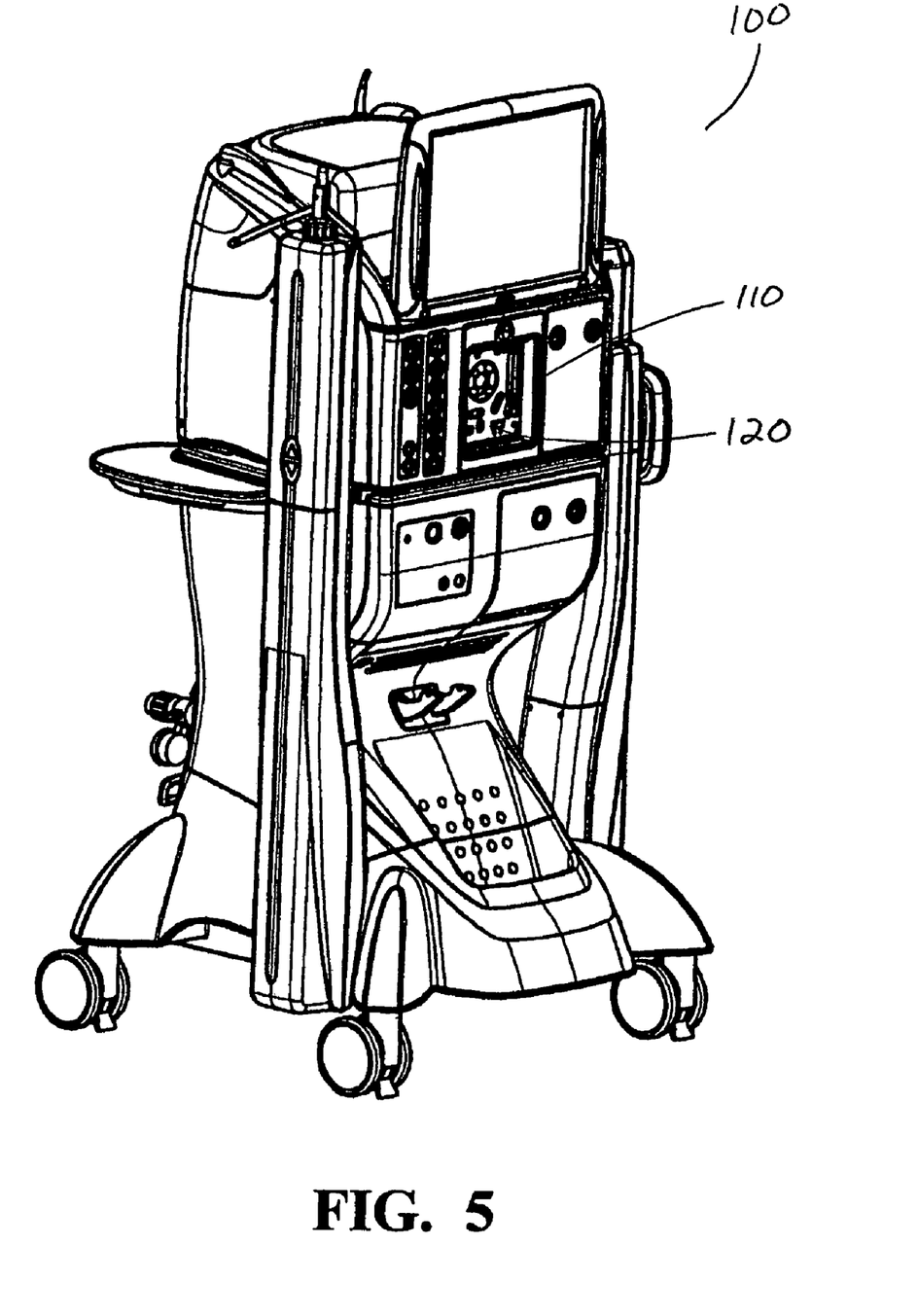
FIG. 5 is a front perspective view of a surgical console that may be used with the cassette of the present invention.

As best seen in FIGS. 1, 2 and 3, cassette 10 of the present invention generally included valve plate 12, body 14 and cover 16. Valve plate 12, body 14 and cover 16 may all be formed of a suitable, relatively rigid, thermoplastic. Valve plate 12 contains a plurality of openings 18 and pumping channel 20 that are sealed fluid tight by elastomers 22 and 24, forming a plurality of fluid paths. Ports 26 provide connectors between cassette 10 and surgical console 100 for the various irrigation and aspiration functions of cassette 10, such functions may requiring the use of filter 28. Attached to body 14 are ultrasound reflector 30 and reflector cover 32. Acoustic reflector 30 and reflector cover 32 may be molded as one piece and are located on body 14 to align with transmission window 125 in recess 36 along fluid passage 34 formed in valve plate 12 when valve plate 12 is assembled onto body 14 in the manner shown in FIG. 3. Located within recess 36 on valve plate 12 is elastomeric acoustic coupler 38. Recess 36 is located adjacent to fluid passage 34 in valve plate 12 and aligned with acoustic reflector 30 and reflector cover 32 when valve plate 12 is assembled on body 14. When cassette 10 is installed in cassette receiving portion 110 of console 100, ultrasound transducer 120 presses against elastomeric acoustic coupler 38, providing an acoustic coupling between transducer 120 and fluid passage 34, thus allowing the use of ultrasound transducer 120 to measure the fluid flow rate in fluid passage 34. Elastomeric acoustic coupler 38 preferably is formed by over molding an elastomeric material, such as a thermoplastic elastomer or silicone rubber within recess 36 of valve plate 12. Such a construction method eliminates the need for adhesives to attach elastomeric acoustic coupler 38 to valve plate 12 and ensures the removal of any air from between elastomeric acoustic coupler 38 and valve plate 12.

Figure 6:
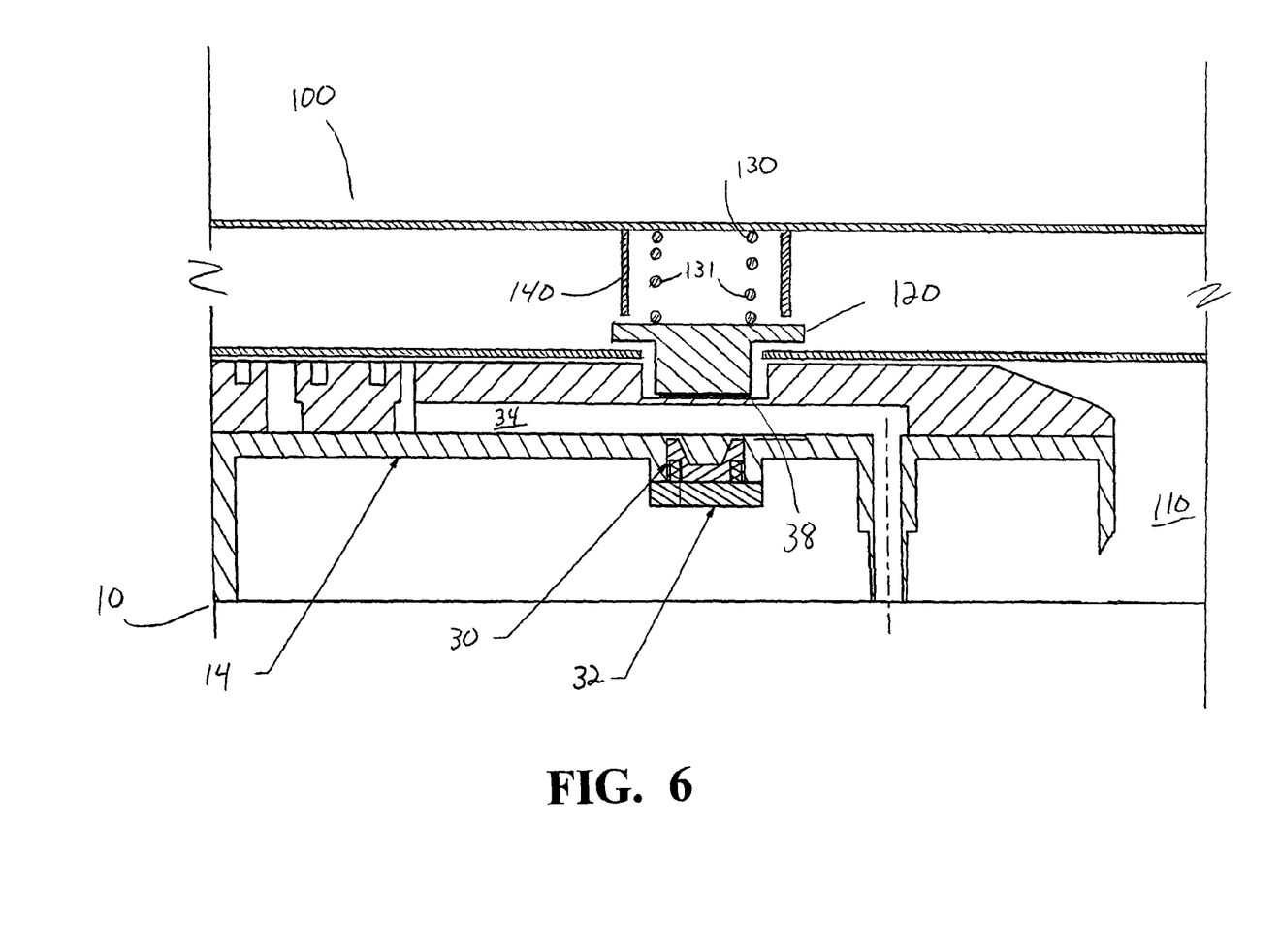
FIG. 6 is a partial cross-sectional view of the cassette installed within a console that may be used with the present invention.

As best seen in FIG. 6, transducer 120 is mounted within cassette receiving portion 110 of console 100 so as to press against coupler 38 when cassette 10 is installed within cassette receiving portion 110. In order to ensure a relatively uniform compressive force by transducer 120 against coupler 38, transducer 120 is mounted within cassette receiving portion 110 on elastic mounting 130, such as spring 131. Mounting 130 preferably has a fairly low spring rate and is compressed through a fairly large deflection, resulting in a force versus position curve having a fairly flat slope.

One skilled in the art will recognize that the description given above is only a schematical illustration of the device of the present invention. For example, instead of spring 131, other similar devices, such as a low friction air cylinder, a solenoid, a motor or an elastomer molded to act like a spring may also be used.

Figure 7:
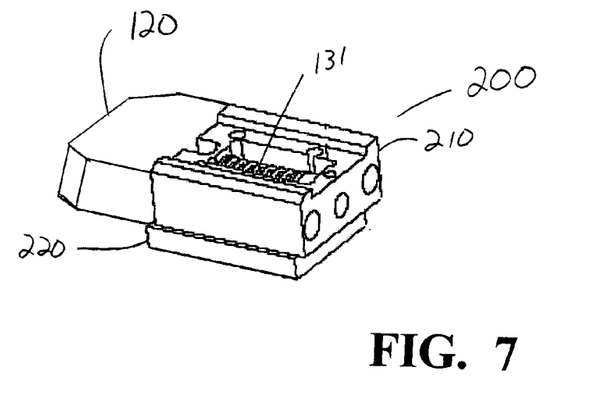
FIG. 7 is a perspective view of an ultrasonic transducer assembly that may be used with the present invention.
Figure 8:
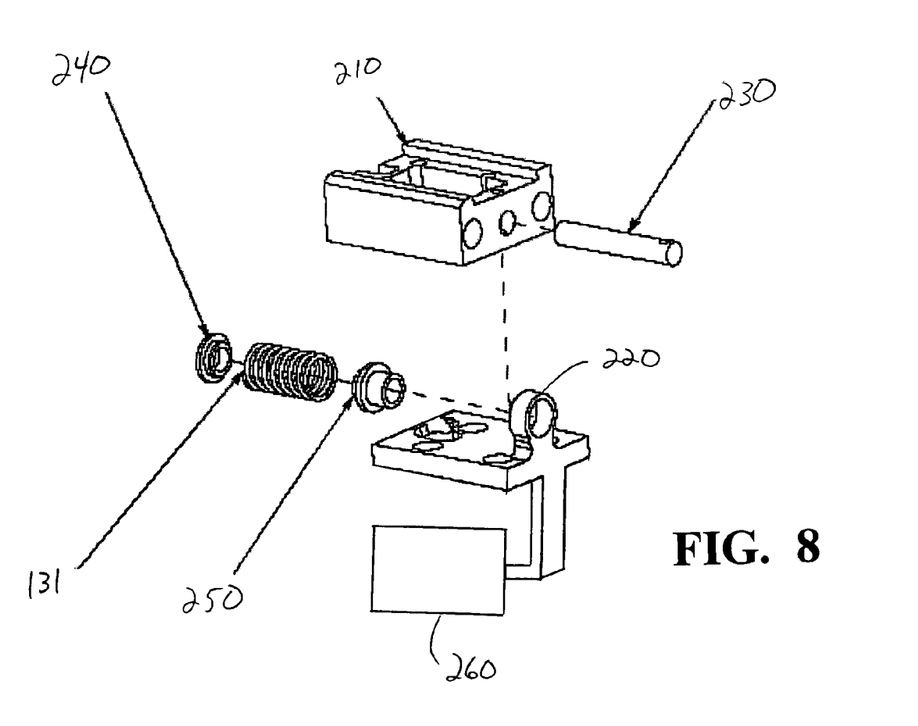
FIG. 8 is an exploded assembly view of the ultrasonic transducer assembly illustrated in FIG. 7.

As best seen in FIGS. 7 and 8, transducer 120 may be mounted on carriage 200. Carriage 200 generally includes carrier 210 mounted to bracket 220. Spring 131 rides on shaft 230 and contains bushings 240 and 250. The construction of carriage 200 is such that transducer 120 can slide within carrier 210 by compressing spring 131. As best seen in FIG. 8, bracket 220 can be mounted to active deployment mechanism 260, such as an air cylinder, solenoid or electric motor, which moves carriage 200 back and forth along the same axis of movement as transducer 120. Active deployment mechanism 260 allows transducer 120 to be retracted within cassette receiving portion 110 when not in use. Retracting transducer 120 helps to prevent damage to transducer 120, which contains delicate crystals that can be damaged easily.

This description is given for purposes of illustration and explanation. It will be apparent to those skilled in the relevant art that modifications may be made to the invention as herein described without departing from its scope or spirit.

We claim:

1. A surgical system, comprising:
    a surgical cassette, comprising:
        a plurality of fluid passages;
        a recess formed along a fluid passage of the plurality of fluid passages, wherein the recess includes an elastomeric acoustic coupler and at least one transmission window; and
        an ultrasound reflector aligned with the at least one transmission window in the recess; and
    a surgical console configured to control aspiration and irrigation through the surgical cassette, the surgical console having a cassette receiving portion; and
    an ultrasonic transducer located in the cassette receiving portion of the surgical console, the ultrasonic transducer configured to measure fluid flow in the fluid passage of the surgical cassette, when the cassette is installed in the cassette receiving portion of the console, the ultrasonic transducer being mounted in the cassette receiving portion by an elastic mount configured to apply a force to push the ultrasonic transducer against the elastomeric acoustic coupler.

2. The surgical system of claim 1 wherein the elastic mount is a spring.

3. The surgical system of claim 1, wherein the acoustic coupler is attached to the cassette by over molding, the acoustic coupler acoustically coupling the ultrasonic transducer to the cassette when the cassette is installed within the cassette receiving portion of the surgical console.

4. A surgical system, comprising:
    a surgical cassette, comprising:
        a plurality of fluid passages;
        a recess formed along a fluid passage of the plurality of fluid passages, wherein the recess includes an elastomeric acoustic coupler and at least one transmission window; and
        an ultrasound reflector aligned with the at least one transmission window in the recess; and
    a surgical console configured to control aspiration and irrigation through the surgical cassette, the surgical console having a cassette receiving portion; and
    an ultrasonic transducer located in the cassette receiving portion of the surgical console, the ultrasonic transducer configured to measure fluid flow in the fluid passage of the surgical cassette, when the cassette is installed in the cassette receiving portion of the console, the ultrasonic transducer being mounted in the cassette receiving portion by an active deployment mechanism, the active deployment mechanism including an elastic mount for the ultrasonic transducer configured to apply a force to push the ultrasonic transducer against the elastomeric acoustic coupler; and
    a carriage, wherein the ultrasonic transducer is mounted on the carriage, and wherein the carriage comprises:
        a carrier; and
        a bracket, wherein the carrier is mounted to the bracket;
    wherein the ultrasonic transducer can slide within the carrier, wherein the bracket is mounted to the active deployment mechanism and wherein the active deployment mechanism is configured to move the carriage.

5. The surgical system of claim 4 wherein the active deployment mechanism further comprises an air cylinder.

6. The surgical system of claim 4 wherein the active deployment mechanism further comprises an electric motor.

7. The surgical system of claim 4 wherein the active deployment mechanism further comprises a solenoid.

8. The surgical system of claim 4, wherein the acoustic coupler is attached to the cassette by over molding, the acoustic coupler acoustically coupling the ultrasonic transducer to the cassette when the cassette is installed within the cassette receiving portion of the surgical console.

9. The surgical system of claim 4 wherein the ultrasonic transducer is attached to the active deployment mechanism by an elastic mount.

10. A surgical system, comprising:
    a surgical console configured to control aspiration and irrigation through a surgical cassette, the surgical console having a cassette receiving portion;
    the surgical cassette having a plurality of fluid passages and an acoustic coupler that is attached to the cassette by over molding;
    an ultrasonic transducer located in the cassette receiving portion of the surgical console, the ultrasonic transducer configured to measure fluid flow in a fluid passage in the cassette when the cassette is installed in the cassette receiving portion of the console, and wherein an ultrasonic transducer is mounted at a right angle to the fluid passage such that the ultrasonic energy from the ultrasonic transducer travels perpendicular to the fluid in the fluid passage;

an active deployment mechanism for mounting the ultrasonic transducer within the cassette receiving portion of the console, the active deployment mechanism including an elastic mount for the ultrasonic transducer; and a carriage, wherein the ultrasonic transducer is mounted on the carriage, and wherein the carriage comprises:
  a carrier; and
  a bracket, wherein the carrier is mounted to the bracket;
wherein the ultrasonic transducer can slide within the carrier, wherein the bracket is mounted to the active deployment mechanism and wherein the active deployment mechanism is configured to move the carriage.

11. The surgical system of claim 10 wherein the active deployment mechanism further comprises an air cylinder.

12. The surgical system of claim 10 wherein the active deployment mechanism further comprises an electric motor.

13. The surgical system of claim 10 wherein the active deployment mechanism further comprises a solenoid.

14. The surgical system of claim 1, wherein the surgical cassette further comprises a valve plate, wherein the valve plate comprises a plurality of openings sealed fluid tight by at least one elastomer to form at least one fluid passage of the plurality of fluid passages.

15. The surgical system of claim 14, wherein the body further comprises a reflector cover to cover the ultrasound reflector on the body.

16. The surgical system of claim 2, wherein the elastic mount further comprises a shaft, wherein the spring is configured to ride on the shaft.

17. The surgical system of claim 4, wherein the active deployment mechanism is configured to retract the transducer within the cassette receiving portion when not in use.

18. The surgical system of claim 10, wherein the active deployment mechanism is configured to move the carriage back and forth along a same axis of movement as the transducer to retract the transducer within the cassette receiving portion when not in use.

19. The surgical system of claim 1, wherein an ultrasound pathway between the ultrasonic transducer and the ultrasound reflector is perpendicular to the fluid passage between the ultrasonic transducer and the ultrasound reflector.

20. The surgical system of claim 4, wherein an ultrasound pathway between the ultrasonic transducer and the ultrasound reflector is perpendicular to the fluid passage between the ultrasonic transducer and the ultrasound reflector.

* * * * *